US00PP29909P2

(12) United States Plant Patent
Van Swieten

(10) Patent No.: US PP29,909 P2
(45) Date of Patent: Nov. 27, 2018

(54) ***PHALAENOPSIS* ORCHID PLANT NAMED 'PHALGLAZAL'**

(50) Latin Name: ***Phalaenopsis* hybrid**
Varietal Denomination: PHALGLAZAL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,844

(22) Filed: Aug. 14, 2017

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGLAZAL', particularly characterized by having large, fresh yellow flowers with a bright yellow lip, 1 to 3 peduncles that are long and moderate, leaves that are oblong, and is propagated by meristem tissue culture, is disclosed.

3 Drawing Sheets

Genus and species: *Phalaenopsis* hybrid.
Variety denomination: 'PHALGLAZAL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGLAZAL'.

The new *Phalaenopsis* plant is a product of a planned breeding program conducted by the inventor in Bleiswijk, The Netherlands. The objective of this breeding program was to create a new *Phalaenopsis* plant with numerous attractive and unique large, fresh yellow flowers with a bright yellow lip, suitable for potted plant production.

The new *Phalaenopsis* plant 'PHALGLAZAL' is a result of cross-pollination made by the inventor in February 2008 in Bleiswijk, The Netherlands of the proprietary female, or seed parent, *Phalaenopsis* hybrid '01-1988' (unpatented) with the proprietary male, or pollen parent, *Phalaenopsis* hybrid '24245-01' (unpatented).

The new *Phalaenopsis* was selected by the inventor as a single plant within the progeny of the stated cross-pollination in a controlled greenhouse in Bleiswijk, The Netherlands in April 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGLAZAL' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALGLAZAL' as a new and distinct variety of *Phalaenopsis* plant.

1) Large, fresh yellow flowers with a bright yellow lip;
2) 1 to 3 peduncles;
3) Peduncle is long and moderate; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in May 2017. Colors in the photographs may differ from the color values cited in the detailed botanical description, which accurately describe the actual colors of the new variety.

DESCRIPTION OF THE NEW VARIETY

Figure 1:
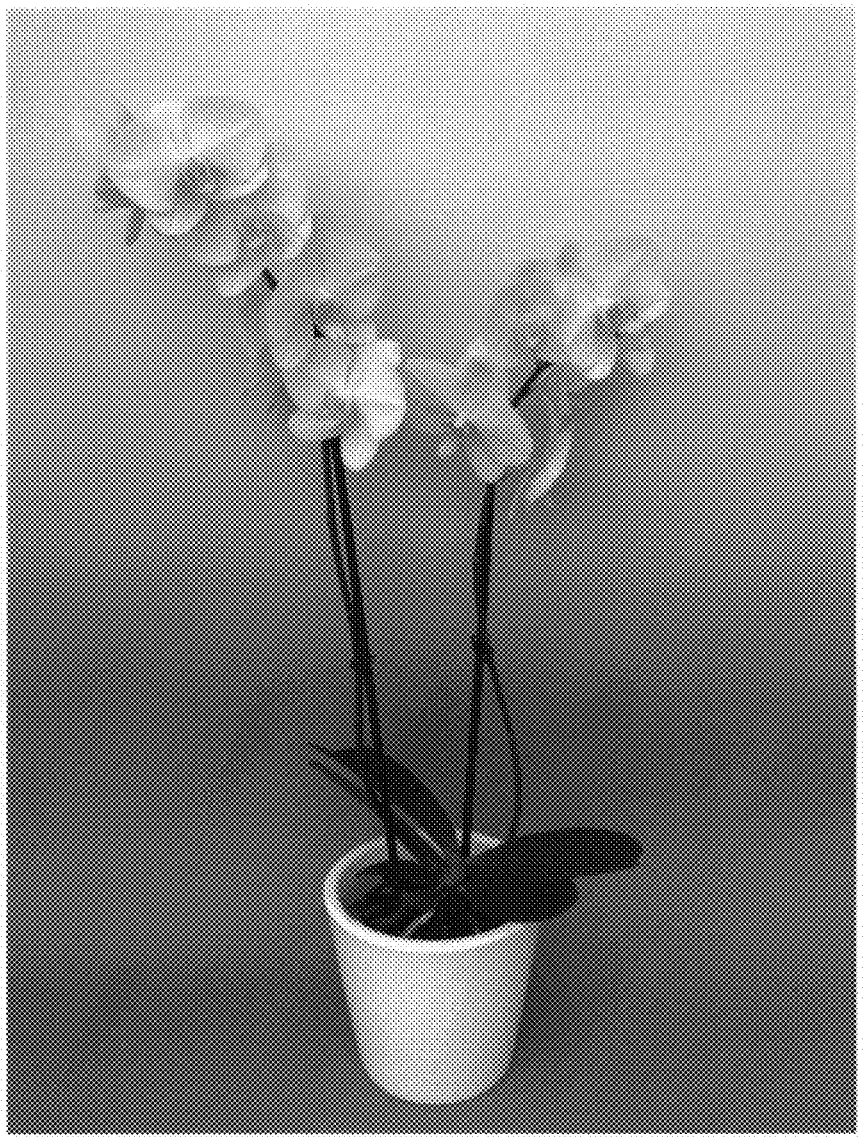
FIG. 1 shows the overall plant habit, including blooms and foliage of 'PHALGLAZAL'.
Figure 2:
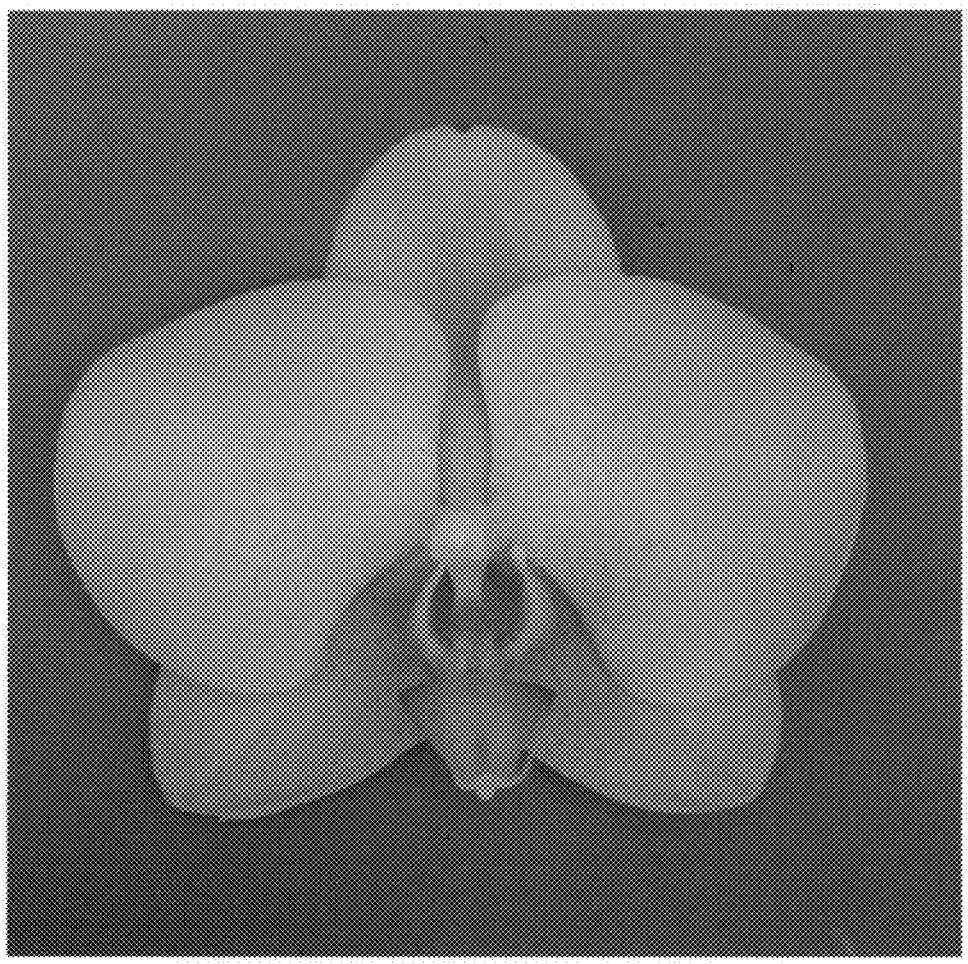
FIG. 2 shows a close-up of a flower of 'PHALGLAZAL'.
Figure 3:
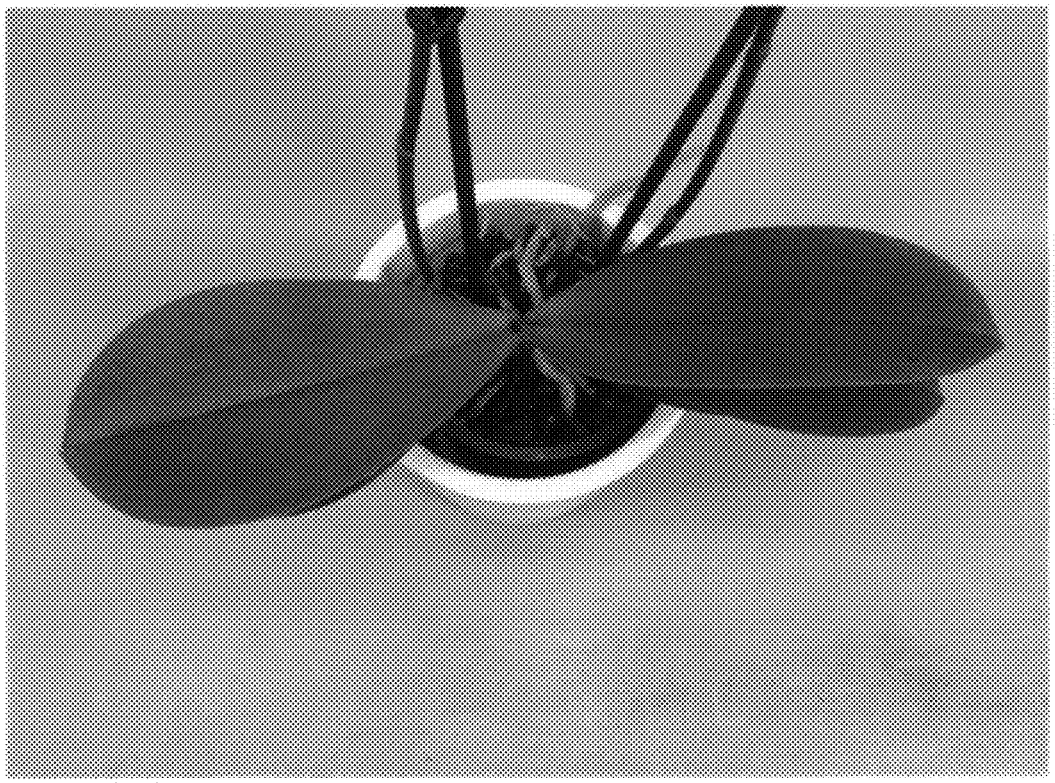
FIG. 3 shows a close-up of the leaves of 'PHALGLAZAL'.

The following detailed description sets forth the distinctive characteristics of 'PHALGLAZAL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in May 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGLAZAL'.

Parentage:

*Female parent*.—*Phalaenopsis* cultivar '01-1988' (unpatented).

*Male parent*.—*Phalaenopsis* cultivar '24245-01' (unpatented).

Propagation:

*Type*.—Meristem tissue culture.

Roots:

*Root description*.—Greyed-green colored roots (RHS 190B) with branching lateral roots having light green colored root tips (RHS 190C).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height (from soil level to top of inflorescence)*.—Approximately 49.0 cm to 59.0 cm.

*Width (measured from leaf tips)*.—About 28.0 cm to 30.0 cm.

*Vigor*.—Moderate.

Leaves:

*Mature leaves*.—Quantity per plant: 5 to 8 leaves are produced before flowering. Length (fully expanded): 14.0 cm to 17.0 cm. Width: 6.5 cm to 7.5 cm. Shape: Oblong. Base shape: Moderately elongated. Apex: Slightly obtuse unequal to rounded. Leaf blade angle with the petiole (measured from the horizontal position): Between 10 degrees and 25 degrees. Leaf margin: Entire. Color: Upper surface: RHS 146A. Lower surface: RHS 146B. Texture: Rough. Thickness: 1.9 mm to 2.2 mm. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—8 to 14.

*Length*.—49.0 cm to 59.0 cm.

*Diameter*.—4.4 mm to 4.9 mm.

*Strength*.—Moderate.

*Aspect*.—Upright to slightly pendant.

*Texture*.—Smooth.

*Color*.—Green (RHS 146A/B) and slightly brown (RHS 200C) at the base.

*Internode length*.—4.5 cm to 5.5 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 170.0 mm to 210.0 mm.

*Flowering time*.—First flowers can be expected 10 to 11 months after planting in a 12 cm (diameter) pot.

*Flower*.—Height: 73.0 mm to 78.0 mm. Diameter: 83.0 mm to 88.0 mm. Depth of lip: 21.0 mm to 23.0 mm.

*Flower longevity*.—On the plant: 6 to 12 weeks.

*Fragrance*.—Absent.

*Flower bud*.—Average size: Large. Length: 24.0 mm to 26.0 mm. Width: 18.0 mm to 20.0 mm. Shape: Egg shaped. Color: Light green (RHS 150B/C).

*Petals*.—Arrangement: Open/free. Shape: Semi-circular. Apex: Rounded asymmetric. Margin: Slightly undulated. Length (from base to tip): 39.0 mm to 41.0 mm. Width: 47.0 mm to 49.0 mm. Color (when fully opened): Upper surface: Basic color: Light yellow (RHS 1D). Over color: Very small dots (RHS 177C). Lower surface: Basic color: Light yellow (RHS 1D). Over color: Absent.

*Dorsal sepal*.—Shape: Broad elliptic. Apex: Emarginated. Margin: Entire. Length (from base to tip): 44.0 mm to 46.0 mm. Width: 34.0 mm to 36.0 mm. Color (when fully opened): Upper surface: Basic color: Light yellow (RHS 1D). Over color: Light yellow (RHS 1C) and very small dots (RHS 177C). Lower surface: Basic color: Light yellow (RHS 1D). Over color: Light yellow (RHS 1C).

*Lateral sepals*.—Shape: Broad ovate. Apex: Obtuse asymmetric. Margin: Entire. Length (from base to tip): 43.0 mm to 45.0 mm. Width: 31.0 mm to 33.0 mm. Color (when fully opened): Upper surface: Basic color: Light yellow (RHS 1C). Over color: Very small dots (RHS 177C). Lower surface: Basic color: Light yellow (RHS 1C). Over color: Yellow stripe (RHS 1B) toward the apex.

*Labellum (lip)*.—Whiskers: Present. Length of whiskers: 7.0 mm to 9.0 mm. Color of whiskers: Light brown (RHS N167A). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Slightly undulated. Length: 16.0 mm to 18.0 mm. Width: 8.0 mm to 10.0 mm. Color: White (RHS NN155A) with light brown (RHS N167B) stripes at the base and yellow (RHS 14B) edge.

*Apical lobe*.—Shape: Rhombic. Margin: Entire. Length: 16.0 mm to 18.0 mm. Width: 17.0 mm to 19.0 mm. Color: Yellow (RHS 13C); brown (RHS 172A) in the middle and at the edge (RHS 172C).

*Callus*.—Average size: Medium. Height: 5.0 mm to 6.0 mm. Length: 4.0 mm to 5.0 mm. Width: 4.0 mm to 5.0 mm. Color: Yellow-orange (RHS 23A) with small brown dots (RHS 172A).

Reproductive organs:

*Column*.—Length: 7.0 mm to 9.0 mm. Diameter: 5.4 mm to 5.7 mm. Color: White (RHS NN155C) and very light purple (RHS 76C) at the base.

*Pollinia*.—Quantity: 2. Diameter: 1.1 mm to 1.3 mm. Color: Orange-yellow (RHS 23A).

*Ovary*.—Length: 6.0 mm to 8.0 mm. Diameter: 2.3 mm to 2.5 mm.

*Pedicel*.—Length: 29.0 mm to 31.0 mm. Diameter: 2.7 mm to 2.9 mm. Color: Light green at the base (RHS 145B); lighter green (RHS 145C/D) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL LINES AND MOST SIMILAR VARIETIES

'PHALGLAZAL' differs from female parent plant '01-1988' (unpatented) in that 'PHALGLAZAL' has yellow flowers, weakly spatulate lateral lobes and a moderately raised callus, whereas '01-1988' has white flowers, spatulate lateral lobes and a strongly raised callus. Additionally, 'PHALGLAZAL' has smaller flowers and much shorter whiskers than '01-1998'.

'PHALGLAZAL' differs from male parent plant '24245-01' (unpatented) in that 'PHALGLAZAL' has yellow (RHS 1D) flowers, weakly spatulate lateral lobes and a moderately raised callus, whereas '24245-01' has yellow (RHS 9A/B) flowers, oblong lateral lobes and a slightly raised callus. Additionally, 'PHALGLAZAL' has much larger flowers and much longer whiskers than '24245-01'.

'PHALGLAZAL' is most similar to the commercial *Phalaenopsis* plants named 'PHALFIMWAQ' (U.S. Plant Pat. No. 26,067) and 'PHALDRAXIP' (U.S. Plant Pat. No. 25,510). 'PHALGLAZAL' differs from the commercial variety 'PHALFIMWAQ' in that 'PHALGLAZAL' has a spotted flower pattern with very small spots, light brown whiskers and rhombic shaped apical lobes, whereas 'PHALFIMWAQ' has a center flower pattern, white whiskers with light yellow tips and triangular shaped apical lobes. Additionally, 'PHALGLAZAL' has shorter apical lobes and wider dorsal sepals than 'PHALFIMWAQ'.

'PHALGLAZAL' differs from the commercial variety 'PHALDRAXIP' in that 'PHALGLAZAL' has entire petal margins, a spotted flower pattern with very small spots and light brown whiskers, whereas 'PHALDRAXIP' has undulated petal margins, a center flower pattern and light yellow whiskers. Additionally, 'PHALGLAZAL' has shorter apical lobes and wider dorsal sepals than 'PHALDRAXIP'.

I claim:

1. A new and distinct variety of *Phalaenopsis* plant named 'PHALGLAZAL', substantially as described and illustrated herein.

* * * * *